United States Patent [19]

Pfeiffer

[11] 4,071,694
[45] Jan. 31, 1978

[54] STETHOSCOPE

[75] Inventor: G. William Pfeiffer, West Lakeland Township, Washington County, Minn.

[73] Assignee: Minnesota Mining and Manufacturing Company, Saint Paul, Minn.

[21] Appl. No.: 719,099

[22] Filed: Aug. 31, 1976

[51] Int. Cl.² ............................................. A61B 7/04
[52] U.S. Cl. .............................. 179/1 ST; 128/2.05 S
[58] Field of Search ................ 179/1 ST; 128/2.05 S, 128/2 K

[56] References Cited

U.S. PATENT DOCUMENTS

| | | | |
|---|---|---|---|
| 3,087,016 | 4/1963 | Dahl | 179/1 ST |
| 3,160,708 | 12/1964 | Andries | 179/1 ST |
| 3,247,324 | 4/1966 | Cefaly | 179/1 ST |
| 3,539,724 | 11/1970 | Keesee | 179/1 ST |

Primary Examiner—William C. Cooper
Assistant Examiner—Kenneth A. Chayt
Attorney, Agent, or Firm—Cruzan Alexander; Donald M. Sell; Edward T. Okubo

[57] ABSTRACT

A combination acoustic and electronic stethoscope which can be operated with one hand is disclosed. The stethoscope has a combination slide valve-electrical switch located in the chestpiece for conversion from an acoustic to an electronic mode of operation. The microphone for the electronic mode is located in the chestpiece and the speaker is located in the Y connector of the earpieces. A volume control and frequency selector control are operative in the electronic mode.

7 Claims, 5 Drawing Figures

STETHOSCOPE

BACKGROUND OF THE INVENTION

The present invention relates to a stethoscope and more particularly to a combination stethoscope having both an acoustic mode and an electronic mode.

The stethoscope has been used for auscultation since its invention in the early nineteenth century. The need for and efforts exerted to develop improved stethoscopes is evidenced at least in part by the many patents which have issued directed to various improvements therein. One direction that improvement has taken has been toward stethoscopes having electronic means for amplifying the sounds produced in the body.

Thus, one finds patents such as Dahl U.S. Pat. No. 3,087,016 which is directed to a combination acoustic and electronic stethoscope consisting of a chestpiece with diaphragm, a hollow handle attached to the chestpiece, and a tube, one end of which is bifurcated for engagement with an operator's ears. Behind the diaphragm is a microphone located in a chamber having an air passage joining the chamber through a hollow bolt to the cavity of the handle. In the air passage is a valve which, on closing, both blocks the air passage and also activates the electronics for operation in the electronic mode. The speaker and batteries are located in the handle cavity. This stethoscope has the disadvantage that when operated in the acoustic mode, sound must travel through the microphone and through the speaker system resulting in attenuation of many frequencies.

Cefaly et al U.S. Pat. No. 3,247,324 discloses a combination acoustic and electronic stethoscope which avoids the attenuation of frequencies inherent in the stethoscope of Dahl by placing just below the position where the tube from a standard chestpiece is bifurcated a housing containing two chambers, one connected to the tube from the chestpiece, the other connected to the tube just below the bifurcation. The chestpiece-chamber has an opening to a microphone and the other chamber has an opening to a speaker. Connecting the two chambers is a tube providing an unimpeded air system from the diaphragm of the chestpiece to the ears of the operator. In this connecting tube is a valve, the operation of which closes the air system and actuates the electronics providing amplification of sound picked up by the microphone and put out by the speaker. Such a stethoscope, though avoiding attenuation of sound, is clumsy and requires two hands to operate.

Keesee U.S. Pat. No. 3,539,724 relates to a combination electronic and acoustic stethoscope which permits selection of the mode of operation by a valve means which, in one position, establishes a passageway directly to the earpieces and in a second position establishes a pathway through an electronic amplifier. Although a stethoscope having such capabilities is desirable and would appear to be technologically feasible, the stethoscope shown and described in the patent would be extremely cumbersome to use.

SUMMARY OF THE INVENTION

The present invention relates to a combination stethoscope which is similar in appearance and size to a conventional acoustic stethoscope yet permits selection of an electronic mode of operation where the physiological sound is amplified by an electronic amplifier as well as the conventional acoustic mode. Selection of the desired mode is effected by means of a combination slide valve-electrical switch located in the chestpiece.

In the acoustical mode the stethoscope operates in the conventional manner without interaction with and unaffected by the electronic amplifier components. In the electronic mode, the body sounds are suitably electronically amplified allowing for control of volume and frequency. Volume control is conventional and is operative only in the electronic mode. Frequency selection is by means of a rotatable three-position selector providing for low, high and mixed frequencies. In the low position, signals above 150 Hz. are increasingly attenuated as are the signals below 150 Hz. when the selector is in the high position. In the mixed position, the entire spectrum about from 20 Hz. to about 2000 Hz. is amplified and transmitted. The frequency selector also has no effect when the stethoscope is in the acoustical mode.

BRIEF DESCRIPTION OF THE INVENTION

In the accompanying drawings which illustrate the invention:

DETAILED DESCRIPTION OF THE INVENTION

Figure 1:
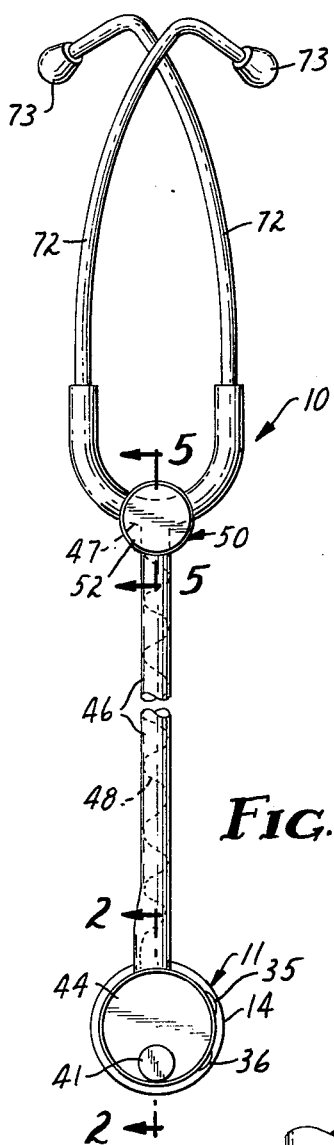
FIG. 1 is a front elevational view of the acoustic/electronic stethoscope of the present invention.

Referring now more particularly to the drawings, the combination acoustic and electronic stethoscope of the present invention is generally indicated at 10 and includes chestpiece 11, a flexible conduit 46 incorporating a Y connector 47 over which rests housing 50 for speaker 60, the Y connector leading to a pair of extension pieces 72—72 at the ends of which are located earpieces 73—73.

Chestpiece 11 comprises a generally cylindrical main housing 12 typically formed of a lightweight metal such as an aluminum alloy although other materials including plastic may be used. One end of housing 12 is covered with an acoustical transducer which takes the form of a diaphragm 13 held to the housing by diaphragm retaining ring 14. Diaphragm 13 is of conventional design and is made from NEMA Grade G-10, .01 inch thick, epoxy resin coated medium glass cloth, double weave.

Housing 12 is also provided with a carrier 15 which fits within the housing and carries the electronic components of the stethoscope thereon and therein. Carrier 15 is preferably formed of two separate plastic parts which are welded together once the electronic components have been assembled.

Carrier 15 is configured adjacent an edge thereof to form an elongated generally rectangular gate valve chamber 17 of gate valve 16. One end of gate valve chamber 7 abuts passage 21 which extends from wall 18 to the center of carrier 15 and terminates in rectangular aperture 22. The other end of gate valve chamber 17 abuts passage 25 which extends from wall 18 to the opposite edge of carrier 15 and terminates in aperture 26. Passages 21 and 25 communicate with each other through apertures 19 provided in wall 18 of gate valve chamber 17. Gate valve piston 20 is configured to snugly slide within gate valve chamber 17. When gate valve piston 20 is in its downmost position, the apertures 19 in wall 18 are blocked by gate valve piston 20 and there is then no interconnection between passages 21 and 25.

Microphone 28 is mounted in carrier 15 along one edge of aperture 22 adjacent to the aperture 29 provided in housing 12. Aperture 29, of course, serves to transmit sound from the diaphragm 13 into the stethoscope for ultimate transmission to the ears of a physician either acoustically or electronically. After the microphone 28 is suitably wired and the conductors are threaded through apertures 30 for interconnection to an amplifier, the two parts forming carrier 15 are welded together. Microphone 28 is thus sealed into the internal air channel of the stethoscope.

The thus assembled carrier 15 is fitted into housing 12 and is suitably secured therein as by gluing to guard against being dislodged and to seal against air leakage. Nipple 31 formed suitably of metal such as aluminum and miniature speaker wire socket 32 are pressed in and secured typically by being glued to carrier 15 through a keyhole aperture 33 in the side wall of housing 12.

A printed circuit (P.C.) board 34 fits onto carrier 15. The P.C. board is provided with mounting sockets on its underside adapted to accept hybrid circuits of conventional design for a low-gain amplifier. A volume control 35 and frequency selector 36 are mounted on the topside of P.C. board 34 and protrude through the side of housing 12 through suitable apertures in the side wall.

The frequency selector 36 is a rotatable selector designed to have three fixed stops, viz., low, high and mixed frequencies. The frequency selector is, of course, inoperative when the stethoscope is used in the acoustical mode. At the low frequency setting, frequencies above approximately 150 Hz. are attenuated as are all frequencies below approximately 20 Hz. The high frequency setting passes all frequencies between approximately 150 Hz. and 2000 Hz. The mixed setting, as the term implies, transmits all frequencies in the range of approximately 20 Hz. to 2000 Hz.

While the frequency ranges of specific body sounds may be the subject of debate, it is generally agreed that the auscultatory sounds occupy a relatively narrow band of the normal human auditory range extending from the lower limits of human hearing, about 20 Hz., to about 2000 Hz. The following Table sets forth the common sounds found in auscultation. It will be noted that the cardiovascular sounds fall in the bottom of the scale in the highly inefficient region of the aural receiving spectrum. Periodic percussive sounds caused by heart valve closures generate the most intense sounds heard through a stethoscope. The frequency spectrum of these sounds is generally concentrated below 150 Hz. To carefully analyze these fundamental heart sounds, it would be desirable to attenuate the higher frequency noises caused by, for example, fluid flow, the respiratory system or mechanical frictional noises of the stethoscope chestpiece against the chest wall. It would also be desirable to reduce the amplitude of the intense low pitched percussive sounds in order to carefully examine the important higher pitched sounds associated with murmurs or with the respiratory system. Thus, separating the high and low frequencies and electronically amplifying body sounds should contribute materially to auscultatory performance.

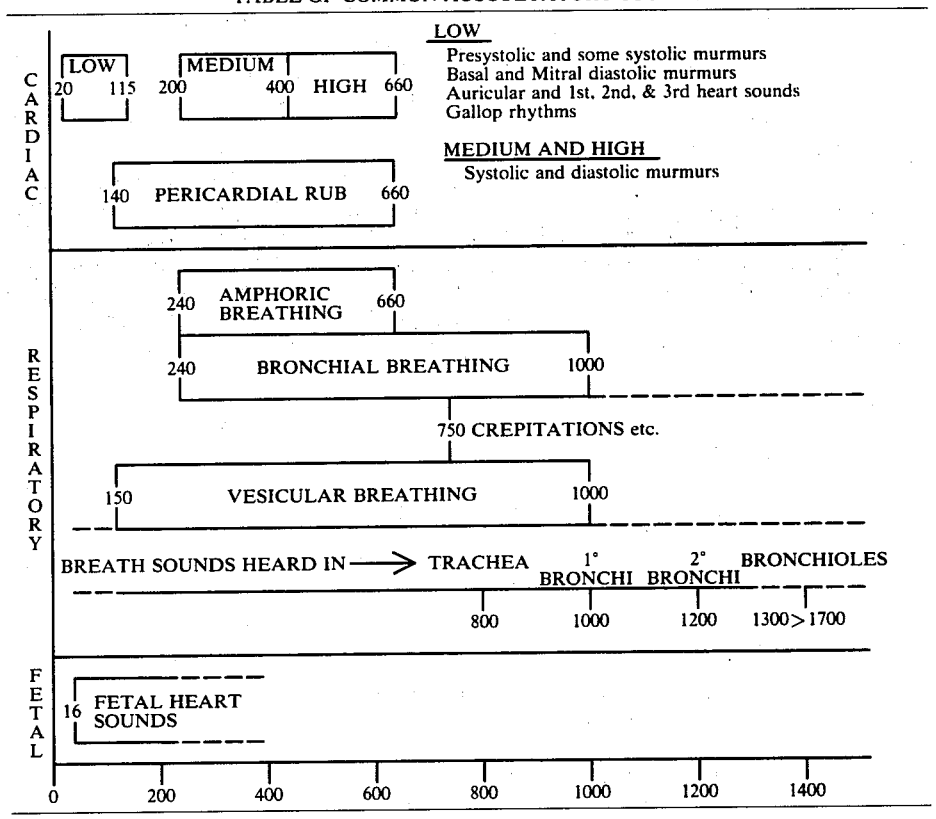

Battery holder 37 formed of an insulating material such as polypropylene is placed on top of P.C. board 34 thus clamping the P.C. board into the housing. In addition to the pair of cavities 38 for batteries 39, battery holder 37 also serves as a cover for the volume control 35 and frequency selector 36 and is appropriately configured to accommodate those controls. Battery holder 37 is also provided with a cylindrical guide sleeve 40 for push button on-off switch 41.

Figure 2:
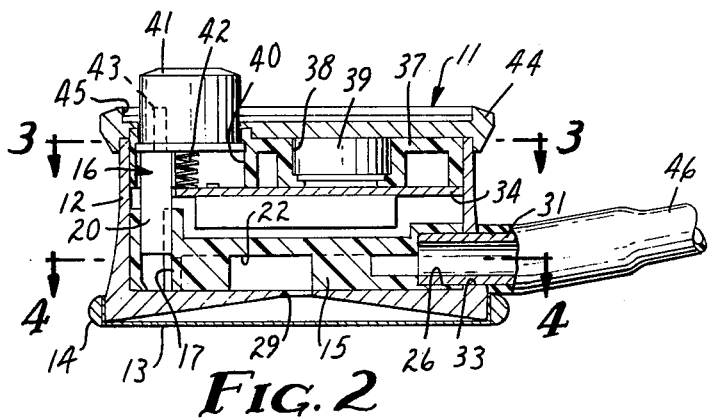
FIG. 2 is an enlarged sectional view of the chestpiece taken along the line 2—2 of FIG. 1.
Figure 3:
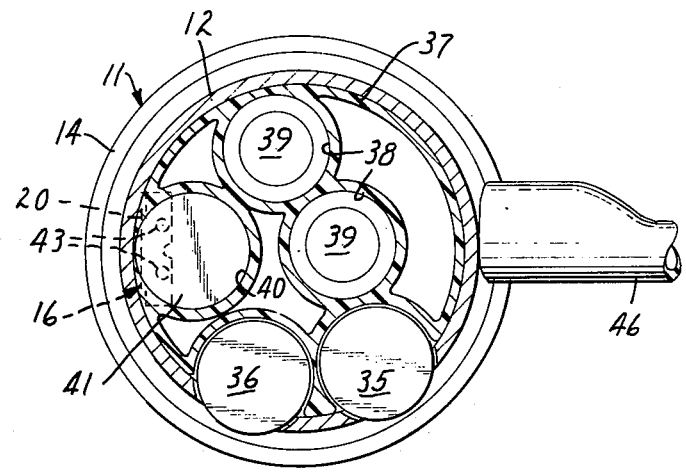
FIG. 3 is a sectional view along the line 3—3 of FIG. 2.

On-off switch 41 is normally spring-biased by helical spring 42 into the "off" position shown in FIG. 2 and is turned "on" when pushed downwardly against spring 42. Although not specifically illustrated in the drawings, one embodiment of the present invention includes an on-off indicator. The indicator is in the form of an indentation in guide sleeve 40 into which a projecting boss on on-off switch 41 drops such that a tactile "click" would be felt by the physician advising him that the stethoscope was in the electronic mode. Surprisingly, the provision of such a tactile indicator greatly minimizes the fatigue which would otherwise be experienced when the stethoscope is used in the electronic mode over an extended period, the tactile "click" apparently serving to assure the physician that the switch has been turned "on" and further incremental pressure is obviously unnecessary. Electrical interconnection is accomplished through contacts located on P.C. board 34 which are closed by button 41. As clearly seen in FIG. 2, switch 41 receives pins 43 projecting from gate valve piston 20 in suitable apertures provided in the underside of switch 41. With gate valve piston 20 thus tied to on-off switch 41, it will be apparent that gate valve piston 20 is normally in the position shown in FIG. 2, in which position, passages 21 and 25 communicate with each other through gate valve chamber 17.

A lid 44 preferably formed of the same lightweight metal as main housing 12 having an opening 45 for push button on-off switch 41 is snap fitted onto main housing 12 to thus seal chestpiece 11.

Flexible conduit 46 is a flexible plastic tubing of polyvinyl chloride approximately fourteen inches long with an inside diameter of 5/32 inch molded into one piece and includes an integral build-in spring. In the fabrication process of flexible conduit 46, a pair of 32 AWG stranded conductors 48 is helically wound around the conduit and exits at a point immediately below the Y connector 47 where they are wired to speaker 60. The flexible conduit 46 also incorporates a miniature speaker wire plug 49 wired to conductors 48 at its free end. It is noted that conductors 48 are wound about conduit 46 and are therefor not within the conduit at any point. Assembly of the flexible conduit 46 and speaker wire plug 49 is accomplished merely by sliding conduit 46 onto nipple 31 and aligning and plugging speaker wire plug 49 with speaker wire socket 32 into mating engagement.

Speaker housing 50, typically formed of plastic and comprising base 51 and cover 52, fits onto flexible conduit 46 at Y connector 47, enclosing both arms and the leg of the Y. Thus, each of base 51 and cover 52 is provided with circumferential slots spaced approximately 120° apart to receive flexible conduit 46 and the arms of the Y connector 47 therewithin. Cover 52 is additionally provided with a vent 53 to permit the diaphragm of speaker 60 to vibrate.

Figure 5:
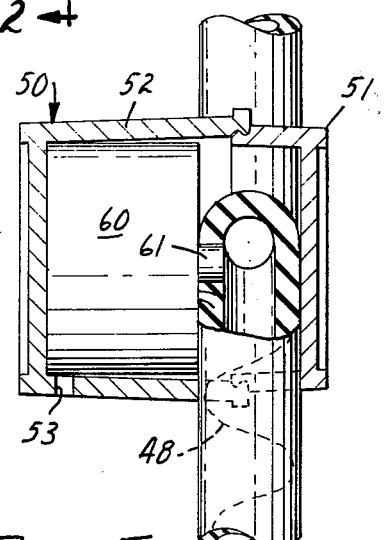
FIG. 5 is a sectional view along the line 5—5 of FIG. 1.
Figure 4:
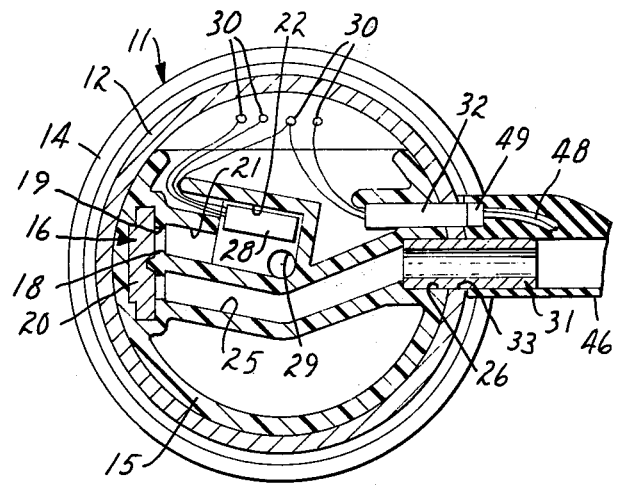
FIG. 4 is a sectional view along the line 4—4 of FIG. 2.

Speaker 60 is carefully chosen so as to have minimum distortion at the frequencies which are diagnostically useful, viz., from about 20 Hz. to 2000 Hz. An especially useful speaker for incorporation into the stethoscope of the present invention had adequate low frequency response at large amplitudes (greater than 100 db. SPL) and minimal effect on the acoustic path. Such a speaker is available commercially from North American Philips under the designation AKG K-2000. As shown in FIG. 5, the output of speaker 60 is through tube 61 which is inserted into flexible conduit 46 from whence the sound output is transmitted via the bifurcated arms of the Y connector 47 to extension pieces 72 at the ends of which are located earpieces 73. Extension pieces 72 and earpieces 73 are all of conventional design.

The following discussion will illustrate the operation of the stethoscope of the present invention:

When the stethoscope 10 is operated in the acoustical mode, push button on-off switch 41 and gate valve piston 20 would be in the "off" position shown in FIG. 2 due to the action of helical spring 42. In this position of the gate valve piston 20, passages 21 and 25 are in communication with each other through gate valve 16 whereby sounds from a body on which the chestpiece 11 is placed cause diaphragm 13 to vibrate generating soundwaves which are conducted through aperture 29, in main housing 12, into aperture 22 in carrier 15 and through passage 21 and into gate valve 16, into passage 25 and out through nipple 31 and through flexible conduit 46, Y connector 47, through extension pieces 72 and finally through earpieces 73 for pickup by the physician. It will be noted that the soundwaves generated by the diaphragm 13 move without obstruction into and through the air passages of the stethoscope chestpiece without being affected in any way by the microphone 28.

In the electronic mode, the push button on-off switch 41 is depressed, thus lowering the gate valve piston 20 and breaking the air passage into two parts which are sealed off from each other. The soundwaves which are generated by the diaphragm 13 again pass through aperture 29 and into rectangular aperture 22 and impinge upon microphone 28 for pickup and subsequent amplification but soundwaves cannot now pass into gate valve 16 due to the presence of gate valve piston 20 therein. Suitable microphones are substantially insensitive to shock and have a frequency response from about 20 Hz. to greater than 2000 Hz. A preferred type of microphone is an electret such as, for example, a "BT-1753" available from Knowles Electronics, Inc. Gate valve 16 is required since speaker 60 drives the air column contained within flexible conduit 46 equally in both directions which would cause feedback to microphone 28 if microphone 28 were not acoustically isolated from speaker 60, the feedback resulting in the familiar high-pitched whine.

Examination of FIG. 1 will show that the stethoscope 10 of the present invention which measures 1.85 inches in diameter and 1.05 inches in height with a weight of 109 g. is very similar in appearance and size to a conventional bell-diaphragm stethoscope. Of thirteen known acoustic stethoscopes measured, the dimensions varied from diameters of 1.57 to 2.35 inches, heights of 0.57 to 1.92 inches and weights of 62 to 280 g. Only upon careful examination would one notice that the main housing 12 was substantially cylindrical and that the traditional bell portion of the stethoscope had been replaced by the lid 44 with push button on-off switch 41 located thereon. A careful observer would also probably notice the presence of speaker housing 50 at the Y connection of the flexible conduit. In all other respects stethoscope 10 resembles a conventional bell-diaphragm acoustical stethoscope.

It has been noted heretofore that the stethoscope of the present invention permits of one-hand operation thus making it possible to switch substantially instantaneously from the acoustic mode to the electronic mode. In this manner, the physician would be able to instantaneously compare an unfamiliar electronically amplified sound with the sound heard in the conventional acoustical mode with which he would be thoroughly familiar.

An additional advantage inherent in any electronic stethoscope resides in the ability to electronically connect to the output of the amplifier. This ability would make it possible for a student or a number of students to listen to the exact sound then being heard by the instructor. It would also be possible to record the sounds on tape or similar recording medium for preservation as a permanent medical history, etc. Although not shown in the drawings, I have constructed a stethoscope having a miniature output socket similar to miniature speaker wire socket 32 wired in parallel to speaker 60 mounted on cover 52. Electrical interconnection was effected with a mating plug and the signal was fed into an audio amplifier with satisfactory results.

What is claimed is:

1. A combination acoustic and electronic stethoscope comprising a chestpiece having an acoustical transducer for picking up body sounds, a passageway coupling said acoustical transducer to a flexible conduit connected to said chestpiece at one end thereof and being bifurcated at the other end thereof, a pair of earpieces connected to said bifurcated conduit to transmit body sounds picked up by said acoustical transducer for listening by a physician, an electronic amplifier for sound amplification and frequency selection, a speaker located at the bifurcation of said conduit and connected to the output of said electronic amplifier, said chestpiece further including an acousto-electronic transducer connected to the input of said electronic amplifier, a power supply interconnected to said electronic amplifier, means for actuating said electronic amplifier to amplify body sounds picked up by said acousto-electronic transducer, said actuating means simultaneously uncoupling said acoustical transducer from said flexible conduit and isolating said acousto-electronic transducer from the output of said speaker, a volume control and a frequency selector operatively connected to said electronic amplifier, said volume control and frequency selector being operative only when said electronic amplifier is actuated to thereby transmit the amplified body sounds through said speaker and earpieces for listening by a physician, said stethoscope being similar in appearance and size to a conventional acoustic stethoscope and being capable of one-hand operation in either an acoustic mode or an electronic mode.

2. A combination acoustic and electronic stethoscope according to claim 1 wherein said actuating means comprises means including a slide valve consisting of a gate valve chamber and a piston sealingly fitting therewithin thereby to interupt the passageway coupling said acoustical transducer to said flexible conduit and for actuating said electronic amplifier.

3. A combination acoustic and electronic stethoscope according to claim 2 wherein said actuating means additionally includes means positively indicating that said electronic amplifier has been actuated.

4. A combination acoustic and electronic stethoscope according to claim 3 wherein said indicating means comprises an indent and a cooperating boss to provide a tactile click.

5. A combination acoustic and electronic stethoscope according to claim 1 including an output jack for receiving signals from said electronic amplifier whereby said amplified signals may be monitored at a location remote from said chestpiece and said earpieces.

6. A combination acoustic and electronic stethoscope according to claim 5 wherein said output jack is located at the bifurcation of the conduit.

7. A combination acoustic and electronic stethoscope according to claim 1 wherein said frequency selector provides for the selection of a plurality of preset frequency ranges.

* * * * *